United States Patent [19]

Hillman

[11] 4,336,223
[45] Jun. 22, 1982

[54] ULTRAVIOLET METHOD FOR DISINFECTION AND STERILIZATION OF FLUIDS

[76] Inventor: Leon Hillman, 141 Pine Ter., Demarest, N.J. 07626

[21] Appl. No.: 141,558

[22] Filed: Apr. 18, 1980

[51] Int. Cl.³ .............................................. A61L 2/10
[52] U.S. Cl. .................... 422/24; 23/230 A; 250/429; 250/430; 250/435; 250/436; 250/437; 422/111; 422/28
[58] Field of Search ............... 422/24, 111, 28; 23/230 A; 250/428, 429, 430, 435, 436, 437

[56] References Cited

U.S. PATENT DOCUMENTS

| | | | |
|---|---|---|---|
| 1,150,117 | 8/1915 | Henri et al. | 250/430 |
| 3,182,193 | 5/1965 | Ellner et al. | 422/24 X |
| 3,566,105 | 2/1971 | Wihrost et al. | 250/430 X |
| 3,837,800 | 9/1974 | Wood | 422/24 |
| 3,948,772 | 4/1976 | Ellner | 422/24 X |
| 4,179,616 | 12/1979 | Coviello et al. | 250/429 X |
| 4,204,956 | 5/1980 | Flatow | 422/24 X |
| 4,255,383 | 3/1981 | Schenck | 422/24 |
| 4,296,066 | 10/1981 | Schenck | 422/111 X |
| 4,302,677 | 11/1981 | Albertsson et al. | 250/429 |
| 4,304,996 | 12/1981 | Blades | 250/435 X |

*Primary Examiner*—Barry S. Richman
*Attorney, Agent, or Firm*—Eugene E. Geoffrey, Jr.

[57] ABSTRACT

An ultraviolet sterilization and disinfection system for fluids which includes apparatus for sensing selected operating characteristics such as physical characteristics of the fluid to be disinfected or sterilized and the operating conditions of the ultraviolet sources proportioning these variable and generally non-linear parameters and modifying such factors as fluid flow, ultraviolet energy imparted to the fluid to insure destruction of selected organisms without the use of excessive energy. Control may also be provided for the admission of selected quantities of disinfecting chemicals such as chlorine to the fluid.

9 Claims, 9 Drawing Figures

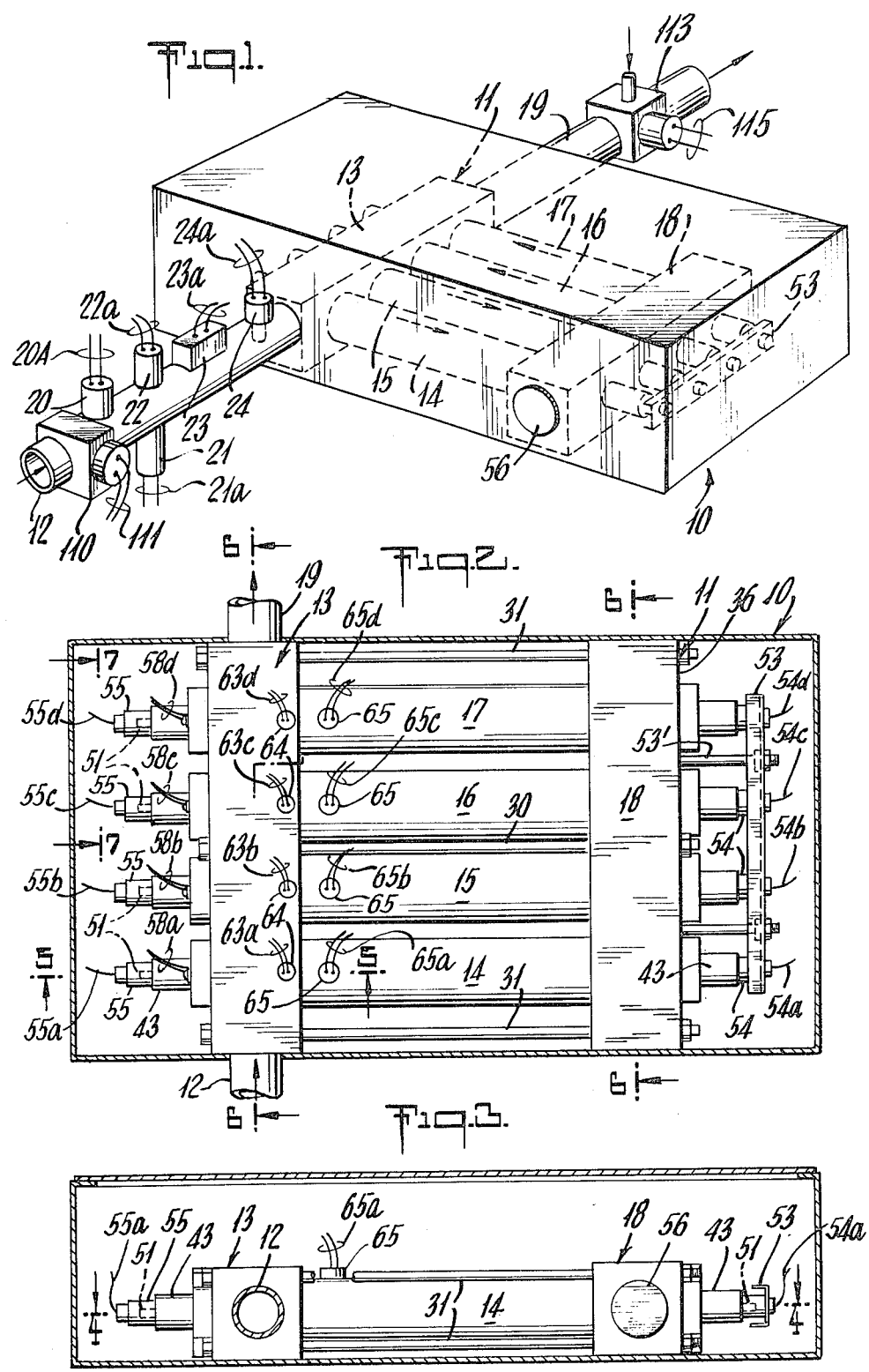

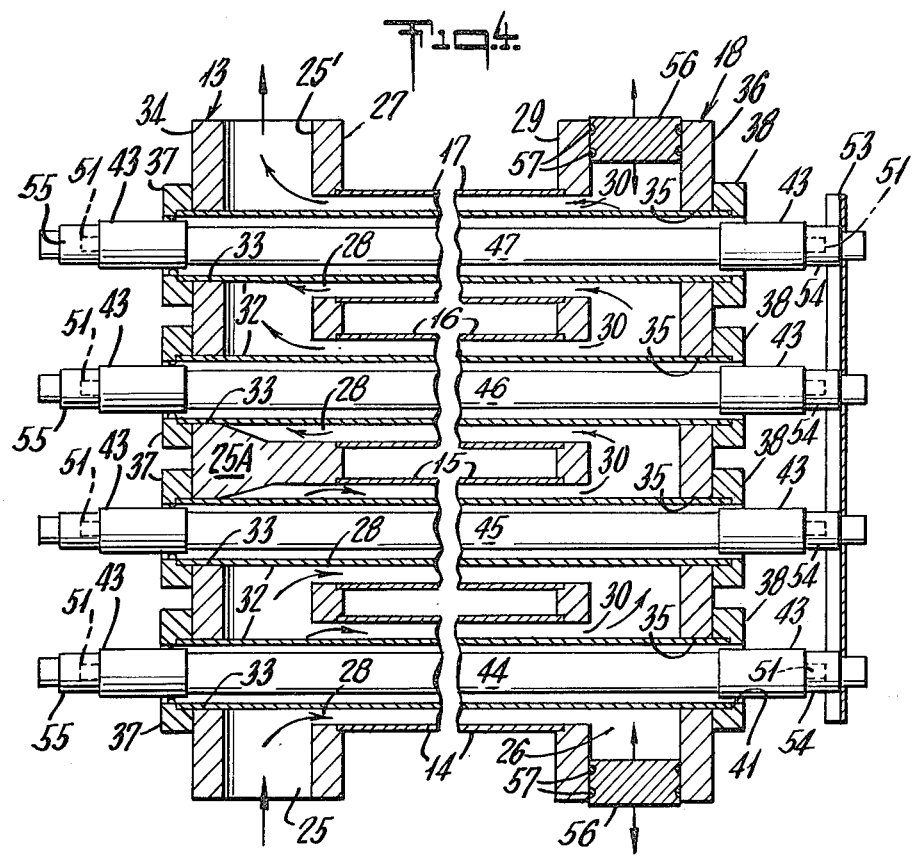
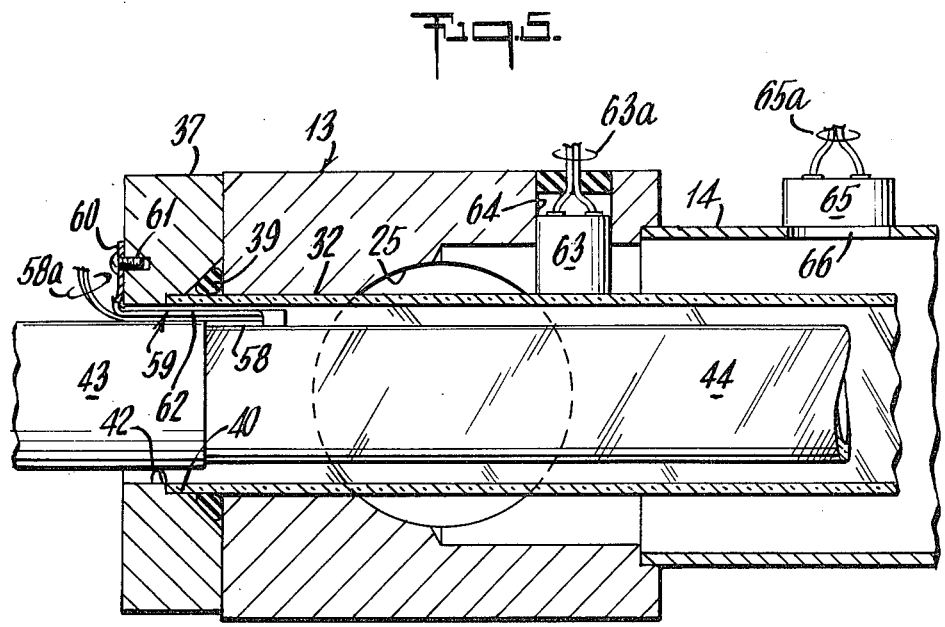

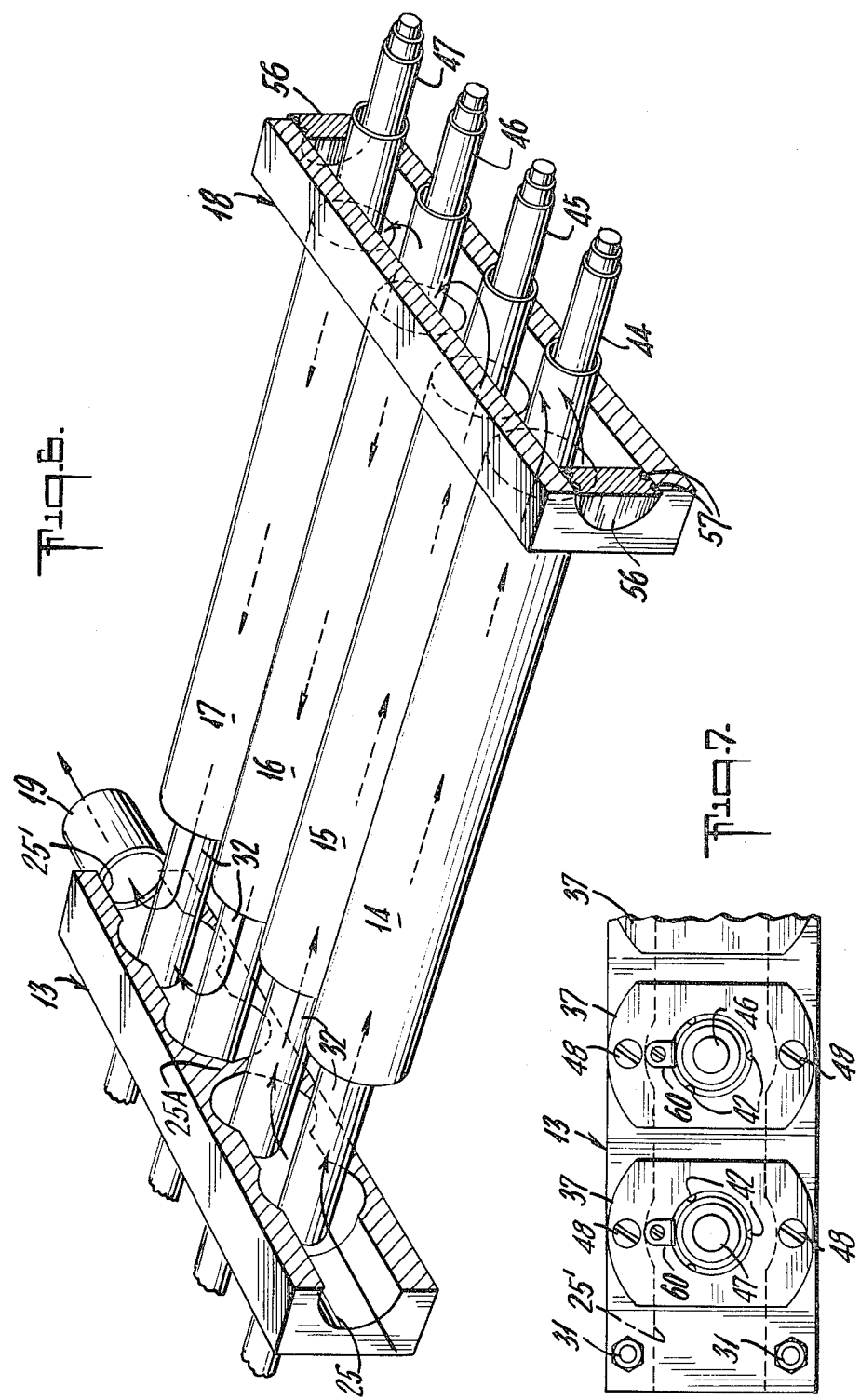

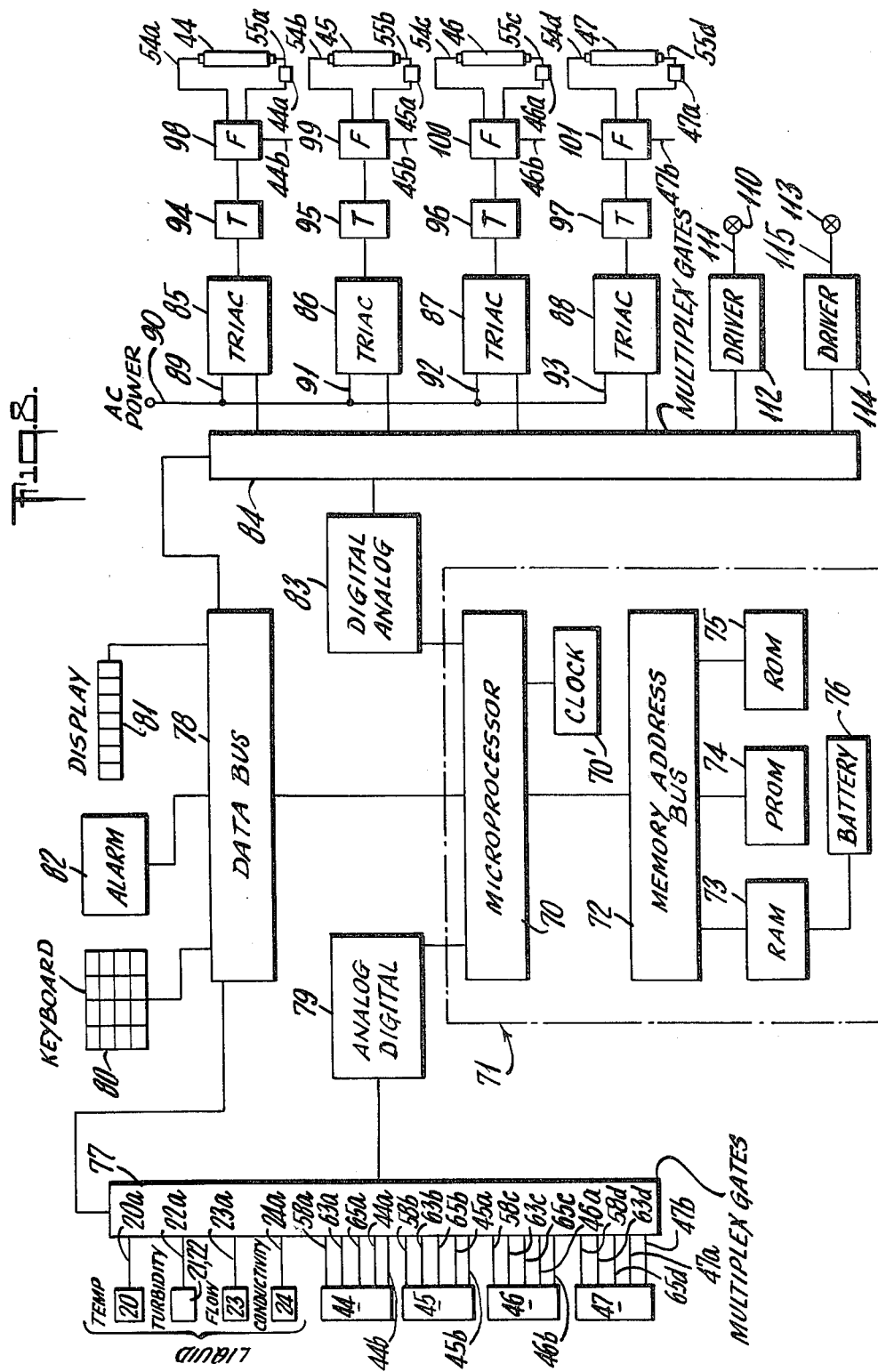

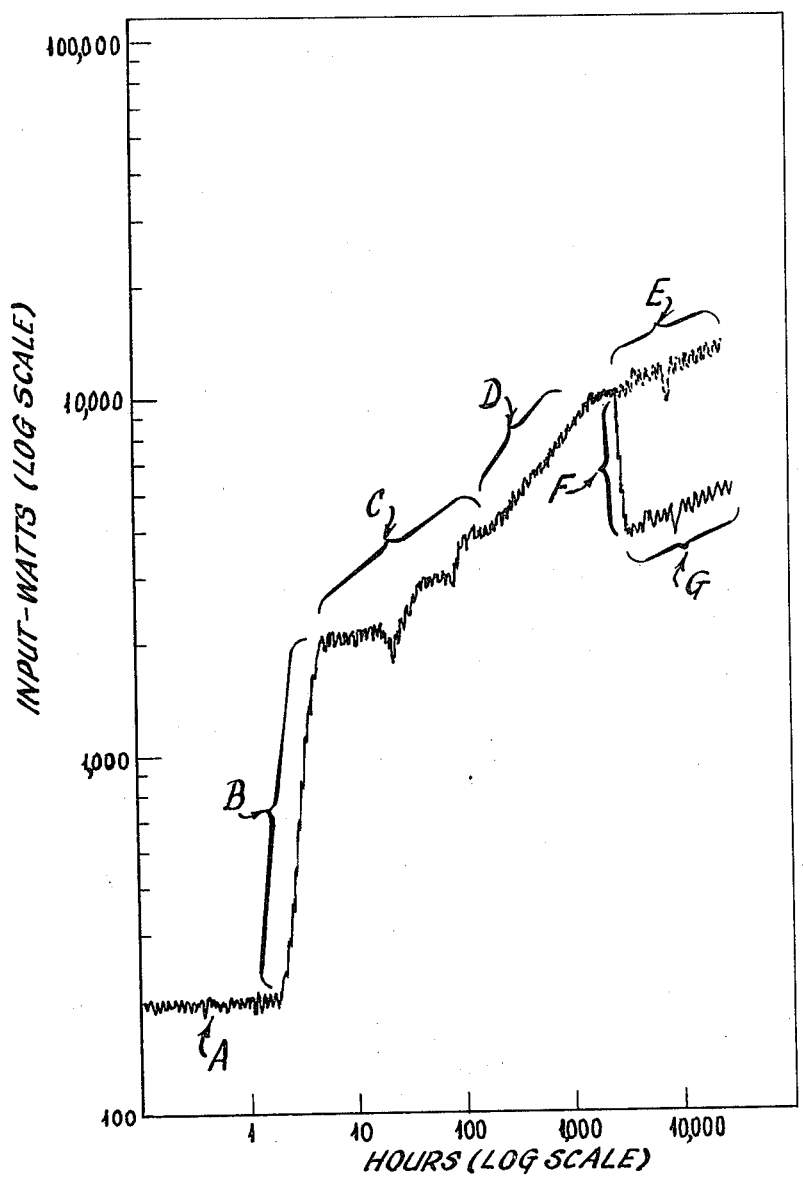

ULTRAVIOLET METHOD FOR DISINFECTION AND STERILIZATION OF FLUIDS

This invention relates to the disinfection and sterilization of fluids and more specifically to a novel and improved method and apparatus for the disinfection and sterilization of fluids utilizing ultraviolet radiation devices which extends the life of such devices, conserves energy and at the same time insures reliable and uniform treatment of the fluids at all times. The invention further contemplates the utilization of controlled chemical treatment in combination with ultraviolet radiation which results in operating efficiencies far in excess of either procedure alone.

The effectiveness of ultraviolet radiation in the sterilization of fluids is well known and a wide variety of systems have been developed for the sterilization of water for both commercial and residential applications. Known ultraviolet sterilization systems are generally of the brute force type limited to specific operating range limits of turbidity, flow rate, temperature and the like to provide ultraviolet exposure considered to be sufficient to insure desired sterilization for at least the major portion of the ultraviolet lamp life. Since the radiation intensity of the ultraviolet lamps decreases with use, known systems are generally designed for proper sterilization near the end of the lamp life with the result that excess operating energy is used when the lamps are new. Furthermore, known systems are designed for specific ranges of turbidity and flow rates to insure satisfactory operation and unexpected changes will result either in failure to properly sterilize or in the use of excessive energy.

The control system in accordance with the invention becomes increasingly important from the standpoint of both reliability and economy in the treatment of lower quality and larger quantities of water. With this invention, lamp life as compared with brute force systems is greatly increased and at the same time substantial reductions in energy requirements are effected. At the same time, great reliability is insured since the required energy (radiation intensity and time of exposure) is imparted to the liquid at all times. Accordingly, this invention has as one of its objects the provision of a novel and improved method and apparatus for the sterilization of fluids which not only insures proper sterilization but also attains that end by controlling lamp power, waveform and starting conditions and modifying lamp power or intensity in accordance with physical conditions, such as flow rate, temperature, turbidity and the like of the fluid. In this way, the apparatus will provide the threshold of energy necessary for the destruction of selected undesirable organisms and viruses over a wide range of fluid characteristics and operating conditions. At the same time, the entire operation can be terminated substantially instantaneously should the ultraviolet radiation source or sources be incapable of imparting the required energy to the fluid.

Another object of the invention resides in the provision of a novel and improved method and apparatus for the sterilization of fluids which not only greatly increases lamp life while affording the ultraviolet energy for the destruction of microorganisms but in instances wherein fluid flow and quality vary over wide limits the conservation of energy through the use of this invention can be a more economical substitute for chemical disinfection treatments than known ultraviolet sterilization methods and apparatus.

Still another object of the invention resides in a novel and improved method and apparatus for the sterilization of fluids and particularly liquids which affords not only increased lamp life but a substantial saving in energy by a continuous modulated control of the energy threshold and exposure as the fluid characteristics, such as flow, turbidity and other conditions change.

Still another object of the invention resides in a novel and improved method and apparatus for the sterilization of fluids wherein the ultraviolet energy imparted to the fluid and/or the rate of flow of the fluid can be controlled to insure proper sterilization. For instance, instead of maintaining uniform flow and modifying the energy imparted to the fluid in accordance with changes in the characteristics of the fluid, the ultraviolet lamps can be operated at maximum intensity and the flow can be controlled to insure proper sterilization.

A further object of the invention resides in the provision of a method and apparatus for the disinfection and sterilization utilizing the combined effects of both chemical and ultraviolet systems. With the novel and improved control system in accordance with the invention, measured quantities of a suitable chemical such as chlorine can be introduced into the liquid depending on the liquid characteristics and flow. With this arrangement, disinfection by the chemical continues beyond the ultraviolet treatment and the combined cost of the chemical and electrical energy is substantially less than the cost of either system alone. In many applications, the resultant cost can be less than 20 to 25 percent of the cost of either system. Thus, not only is considerable economy realized by this synergistic effect but residual chlorine can be maintained within tolerable limits.

The invention comprises a novel and improved ultraviolet sterilization system for sterilization of fluids embodying ultraviolet generating means capable of producing a desired energy threshold and exposure for said fluids under adverse conditions of fluid quality throughout the life of the lamps, means for continuously monitoring at least selected characteristics of the fluid and radiant energy emitted from the generating means, means for modifying the magnitude of ultraviolet radiation in accordance with the monitored characteristics to provide the desired energy threshold and exposure to effect sterilization and controlling the characteristics of the energy supply to the generating means to maximize further the life of the generating means. The invention further provides a system for controlling fluid flow in accordance with changes in fluid characteristics while maintaining ultraviolet energy at a maximum or in the alternative modifying fluid flow if the ultraviolet intensity and exposure time is insufficient to achieve proper sterilization. Means are also provided for controlling the admission of a disinfecting chemical to the liquid in accordance with liquid characteristics while at the same time sterilizing the liquid with controlled ultraviolet radiation.

The above and other objects and advantages of the invention will become more apparent from the following description and accompanying drawings forming part of this invention.

IN THE DRAWINGS

FIG. 1 is a perspective view of one embodiment of the apparatus for the sterilization of fluids utilizing ultraviolet radiation;

FIG. 2 is a plan view of a portion of the apparatus illustrated in FIG. 1;

FIG. 3 is a side elevational view of FIG. 2 with the housing wall removed;

FIG. 4 is a cross sectional view of FIG. 3 taken along the line 4—4 thereof;

FIG. 5 is a cross sectional view of FIG. 2 taken along the line 5—5 thereof;

FIG. 6 is a perspective view of the structure shown in FIG. 2 with sections taken along the lines 6—6, 6—6 thereof;

FIG. 7 is a fragmentary end view of FIG. 2 taken in the direction of arrow 7; and FIG. 8 is a block diagram illustrating the circuitry for controlling the intensity of the radiation produced by the ultraviolet radiation sources.

FIG. 9 graphically represents a typical example of the power demand required to meet variations normally experienced in the ultraviolet sterilization of liquids.

The effectiveness of ultraviolet radiation for the sterilization of fluids and particularly water has been recognized for many years. Known devices utilizing ultraviolet radiation embody appropriate means for the circulation of the liquid in close proximity to ultraviolet lamps in order to expose all of the liquid to the radiation and at the same time provide the desired exposure to effect the destruction of micro-organisms. The design concept of such systems, however, involved the determination of the radiation intensity of the lamps at or near the end of the lamp life and sufficient lamps were provided to obtain the necessary exposure time to effect the desired sterilization. Under those conditions, new lamps therefore afforded radiation intensities far in excess of that required to effect the desired sterilization. Such procedures while being generally satisfactory for use with liquids having known physical and chemical characteristics are not reliable under conditions wherein the characteristics of the liquid are subject to variations. Moreover, even under conditions wherein some control is exercised over the characteristics of the liquid, insufficient radiation may, nevertheless, be experienced particularly toward the end of the normal lamp life. To compensate for such deficiencies in known systems, efforts have been made to insure the provision of radiation intensities and exposure far in excess of that which would be normally required to effect the desired ends. The efficiencies of known systems, therefore, are not only poor as far as energy consumption is concerned but operation of the lamps at maximum intensity at all times also materially shortens the life of the lamps. Moreover, known systems do not provide for unexpected variations of water characteristics, flow rate and the like and should the ultraviolet lamps be nearing the end of their normal life and if water turbidity for instance should change materially, it is most likely that proper sterilization will not be effected. With this invention, however, effective sterilization is insured notwithstanding changes in the water even though they may vary over wide ranges within design limits that may be selected. Should such variations exceed design limits, an alarm can be provided and termination of the process effected. With the method and apparatus according to the invention, sterilization can be attained at a cost competitive with and often far less than chemical treatment.

It is well recognized that a wide variety of structures may be employed for the purpose of subjecting fluids and specifically water to ultraviolet radiation for the purpose of sterilization. One such structure, as illustrated in the drawings, provides for the flow of water lengthwise of elongated ultraviolet radiating lamps though it is evident that the water can be directed transversely of the lamps, so called laminar flow, and that other lamp configurations may be employed.

Referring now to the drawings and more specifically to FIGS. 1 through 7, the illustrated embodiment of the invention includes a housing 10 containing the ultraviolet sterilizing apparatus generally denoted by the numeral 11. The apparatus 11 is shown and illustrated in diagrammatic form in FIG. 1 while in the remaining figures details of the structure are illustrated. Referring to FIG. 1, a water inlet conduit 12 is connected to one side of the header 13. The water then flows to the right through tubes 14 and 15 into the header 18 thence through tubes 16 and 17 for return to the header 13 and discharge through the outlet conduit 19. The inlet conduit 12 includes a plurality of sensors to determine certain physical characteristics of the liquid to be treated. In the instant embodiment of the invention, the temperature sensor 20 having leads 20a extending therefrom records the temperature of the liquid in the inlet. This sensor is followed by a turbidity sensor consisting of a suitable light source 21 having leads 21a extending therefrom for energizing the light source and a photoelectric sensor 22 having leads 22a extending therefrom. The flow detector is denoted by the numeral 23 having leads 23a and the conductivity detector is denoted by the numeral 24 having leads 24a extending therefrom. These measurements made by the sensors are utilized, as will be discussed in connection with FIG. 8, to effect in combination with other measurements, the operation of the ultraviolet radiation sources.

Referring more specifically to FIGS. 2 through 7, the headers 13 and 18 are essentially of rectangular configuration with the header 13 having longitudinal bores 25 and 25' extending inwardly from opposing ends to points spaced from the center to provide a central barrier 25a. The face 27 of the header 13 has four openings each denoted by the numeral 28 for frictionally receiving one end of each of the tubes 14 through 17. A suitable sealing compound may be employed to insure water tight joints. Similarly, the face 29 of the header 18 has a plurality of corresponding openings 30 to receive the opposing ends of the tubes 14 through 17 in like manner. The headers 13 and 18 with the tubes 14 through 17 disposed therebetween are then held in position by a plurality of bolts 31 as viewed more clearly in FIGS. 2 and 3.

Tubular elements formed of quartz or other suitable radiation transparent material and denoted by the numeral 32 extend through each of the tubes 14 through 17 and through cooperating openings 33 in the wall 34 of the header 13 and similarly through openings 35 in the wall 36 of the header 18. It will be observed that the tubes 32 protrude slightly beyond the walls 34 and 36 of the headers 13 and 18 and are held in position by annular caps 37 and 38. Each tubular element 32 is sealed by an O-ring 39 as illustrated more clearly in FIG. 5. More specifically, each of the caps 37 as well as the caps 38 on the header 18 has an enlarged opening 40 for slidably receiving the tubular element 32. The remainder of the opening 41 through each cap 37 and 38 is approximately equal to the inside diameter of the element 32 and the caps 37 each include three or more spacing elements 42 to center tubular lamps 44 through 47 within openings 41 of the caps 37 by engagement with the lamp ferrals 43 on one end of each lamp. Since the ferrals 43 on the other end of each lamp are centered by fixedly positioned sockets, as will be described, air can readily circulate in the space between each lamp and the associated surrounding element 32. Each of the caps 37 and 38 is held in position by screws 48 as will be observed more clearly in FIG. 7.

As previously mentioned, the ultraviolet radiation sources 44 through 47 are in the form of tubular structures having an elongated radiation transparent tube 49 carrying tubular ferrals 43 on each end thereof. Cylindrical terminals 51 extend from each end of each lamp for engagement with sockets as shown in FIGS. 2 and 3. In these figures, it will be observed that an elongated channel member 53 is disposed parallel to the header 18 and carries insulated sockets 54 in spaced relationship to the wall 36 of the header 18. The channel member 53 is held in precisely spaced relationship by a pair of bolts 53'. Each of the sockets 54 is precisely aligned with the axis of the associated radiation transparent tube 32 so that a lamp inserted from the left side of the structure as shown in the figures will frictionally engage the associated socket 54 and thus maintain the lamp in proper position within the apparatus. Similar sockets 55 individually engage terminals 51 on the left end of the ultraviolet lamps as illustrated.

It is often desirable to control the turbulence of the liquid being treated with apparatus in accordance with the invention though it is desirable to avoid devices that will function to impede or otherwise resist the flow of the liquid. In the instant embodiment of the invention, turbulence can be controlled by adjusting the curvatures of the liquid flow path within the headers 13 and 18. In addition, turbulence can also be controlled by utilizing movable closure elements 56 on each end of the header 18. In this instance, it will be observed that the closure 56 are sealed to the inner bore of the header 18 by O-rings 57 and suitable means may be provided for moving the closures 56 inwardly and outwardly of the ends of the header 18. In this way, turbulence can be controlled without imparting any significant resistance to the flow of the liquid through the apparatus.

FIGS. 2, 3, 5 and 7 illustrate additional sensing devices for use in the control of the energy fed to the ultraviolet lamps 44 through 47. It was previously pointed out in connection with FIG. 1 that sensors for measuring liquid, temperature, flow, turbidity and conductivity played important roles in controlling the intensity of ultraviolet radiation and exposure time in order to insure proper sterilization of the liquid. In addition to those factors, it is desirable to measure continuously the operating conditions of the ultraviolet lamps as well as the penetration of the ultraviolet radiation through the liquid surrounding each of the lamps. For instance, measuring the ultraviolet radiation directly from the lamp surface will provide a continuous indication of the intensity of the radiant energy while measurement of the ultraviolet radiation at the surface of the liquid through windows in the liquid conducting tubes 14 through 17 will indicate the degree of absorption of the radiation by the liquid. Insufficient intensity at the surface of the liquid will therefore necessitate either increase in the intensity of the radiation or in the alternative an increase in the exposure time. The temperature at the surface of each lamp will insure proper operation of the lamps. For instance, the temperature of a lamp may change with lamp current and if the lamp temperature should increase beyond a known optimum value, the intensity of the radiation will decrease. Furthermore, lamp temperature provides an indication of ambient temperature conditions which can be adjusted to attain the desired operating temperature for the lamps. Accordingly, lamp temperature constitutes a significant factor and insures efficient operation of the apparatus.

The sensing devices for lamp temperature, intensity of radiation at the surface of the lamp and intensity of radiation at the surface of the liquid are shown in FIGS. 2, 5 and 7. The sensor for measuring lamp temperature is shown more clearly in FIG. 5 and comprises a thermistor 58 or other suitable device carried by an L-shaped bracket 59 having one leg 60 secured to the cap 37 by means of a screw 61 and a second leg 62 extending in the space between the lamp 44 and the surrounding radiation transparent tube 32. The thermistor 58 is carried at the inner end of the leg 62 and the wires 58' from the thermistor 58 would normally be carried by the bracket leg 62 and properly insulated therefrom. The bracket 62 is formed of resilient material so that when the lamp 44 is in place the thermistor 58 will bear tightly against the lamp surface and at the same time the resiliency will permit the lamp to be readily withdrawn for repair or replacement. Lamp intensity is measured by a suitable photo detector 63 carried within an opening 64 in manifold 13. If desired, the radiation intensity sensor 63 may include a suitable filter that will pass only a selected radiation bandwidth found most effective for a selected sterilization process. Any deviation of the lamp from the selected bandwidth will immediately indicate a loss of radiation and this condition can be rectified by proper adjustment of lamp current and/or voltage unless of course the lamp is near the end of its life which factor can also be determined by the relationship of lamp intensity to lamp temperature, current and/or voltage.

The intensity of the radiation at the outer surface of the liquid flowing through the tubes 14 through 17 is measured by a photo detector 65 mounted on the surface of each of the tubes 14 through 17. For this purpose, each of the tubes is provided with a window 66 to which the photo detector or other equivalent device is secured. As in the case of the intensity measuring device 63, the device 65 may also be provided with a suitable filter. In this way, adequate penetration of the liquid by the radiation can be assured throughout the entire sterilizing process.

As previously mentioned, the effectiveness of ultraviolet radiation in the destruction of micro-organisms and viruses is known. It is also known that ultraviolet radiation of the order of 2,537 angstroms is the most effective germicidal wavelength and that ultraviolet energy is generally given in terms of micro-watt seconds per square centimeter. Published information is generally available indicating the total energy required for the destruction of selected micro-organisms and such energy ranges from as low as 1,600 micro-watt seconds per square centimeter for 90 percent effectiveness against certain organisms to as much as 440,000 micro-watt seconds per square centimeter for other organisms for complete colonization destruction. Utilizing known ultraviolet sterilizing systems which are essentially all of the brute force type, the inefficiencies are of such great magnitude that ultraviolet sterilization processes have been restricted by cost effectiveness as compared with known conventional chemical treatments such as treatment utilizing chlorine. With the instant invention however, the apparatus is not only controlled to provide only that power necessary to destroy selected micro-organisms but the adjustment can be modified during operation in the event more or less energy is required for the destruction of the organisms. It has also been found, as previously pointed out, that the life of ultraviolet lamp sources can be more than doubled by controlling both lamp current and voltage to provide only that radiation intensity necessary for achievement of the objects of the apparatus. With this invention, efficiencies of the order of one hundred times those attainable with known apparatus can be achieved and in many cases enables ultraviolet sterilization to be economically competitive with chemical processes. The importance of this invention becomes even more evident upon consideration of the adverse effects of chlorine on the human body not to mention taste when chlorine is utilized for sterilization of drinking water. Chlorine is also being found particularly disadvantageous because of the results of research showing a connection between cancer and chlorination when combined with other chemicals found in water. Further, the cost of chlorine has been constantly increasing, chlorine control presents serious complications both in metering as well as its deleterious affect on water handling equipment.

FIG. 8 shows a block diagram of one circuit for automatically controlling the intensity of radiation from the ultraviolet radiation sources in accordance with the invention. It will be observed that a microprocessor 70 is utilized to perform the basic functions of logic and forms part of the basic control 71 which includes the memory address bus 72, a random access memory (RAM) 73, a programmable read only memory (PROM) 74, a read only memory (ROM) 75 and a clock 70'. A self contained battery 76 is used as a constant standby source for the random access memory.

The information pertaining to the characteristics of the fluid being sterilized or disinfected is fed from the sensors 20, 22, 23 and 24 through the leads 20a, 22a, 23a and 24a to the multiplexing gates 77 and represent temperature, turbidity, flow and conductivity respectively. The blocks 44 through 47 represent the measuring devices associated with the four ultraviolet radiation lamps 44 through 47 and the blocks are denoted by the same numerals utilized to denote the lamps. For instance, the lead 58a coupling the block 44 to the multiplexing gates 77 provides a signal proportional to lamp temperature. The lead 63a provides a signal proportional to intensity of radiation measured at the surface of the radiation transparent element 32, the lead 65a provides a signal proportional to radiation intensity at the surface of the fluid while the leads 44a and 44b provide signals proportional to current and voltage respectively in the lamp 44. The signals from the sensors associated with lamps 45 through 47 are similarly denoted by the subscripts b, c and d respectively except for the lamp current and voltage which leads are denoted by the numerals 45a, 46a, 47a and 45b, 46b and 47b respectively.

The multiplex gates 77 feed information to the data bus 78 and through an analog to digital converter 79 to the microprocessor 70. A keyboard 80 and display 81 are connected to the data bus 78 together with an alarm 82. Lamp control information is fed from the microprocessor 70 through the digital to analog convertor 83 to the multiplex gates 84. There is also a coupling between data bus 78 and the microprocessor 70 to provide for the transmission of information to the microprocessor via the keyboard and for retrieving information for presentation on the digital display 81 and a coupling between the data bus and multiplex gates 84.

The multiplex gates 84 produce lamp control signals which are fed to control devices 85 through 88 such as Triacs or other similar devices. AC power is fed to the Triacs 85 through 88 via the leads 89, 90, 91, 92 and 93 and the power outputs from the Triacs 85 through 88 are fed to ballasts 94 through 97. The ballasts are required for starting the lamps 44 through 47 and maintaining the ionization within each lamp after starting has been completed.

It has been found that the life of ultraviolet lamps is materially affected by the characteristics of the energy utilized for starting the lamp and maintaining its operation. More specifically, sharp transients in the energy applied to ultraviolet lamps materially shorten the life of the lamps and accordingly the energy from each ballast 94 through 97 is each fed through an individual filter 98 through 101 for removal of energy peaks. For this purpose, the filters would be either low-pass or band-pass filters which are tuned to remove all frequencies greater than the frequency of the AC power. The outputs from the filters 98 through 101 are fed through leads 54a and 55a to the lamp 44, 54b and 55b to the lamp 45, 54c and 55c to the lamp 46 and 54d and 55d to the lamp 47. Suitable devices 44a through 47a are interconnected with the leads 55a through 55d to produce current signals which are fed to the multiplexing gates 77. Similarly, voltage signals are obtained from the filters 98 through 101 via the leads 44b through 47b which are also fed to the multiplexing gates 77. In this way, both voltage and current in the lamps can be controlled as it has been found that through careful control of both starting and operating voltages and currents as well as maintenance of a proper waveshape, lamp life can be significantly extended.

It is to be understood that the foregoing block diagram presents only one embodiment of a possible circuit arrangement utilizing a microprocessor for achieving modulated power control of the ultraviolet lamps. As mentioned, the sensors each produce an analog voltage which is adjusted to vary over a predetermined range. The analog and digital converter 79 codes these inputs for transmission to the microprocessor 70. The ROM would preferably be preprogrammed with an executive program which constitutes the basis for the microprocessor functions. The PROM 74 provides for auxiliary functions which may be unique to a particular installation. The input to this memory is by way of the keyboard 80 or other similar alpha-numeric terminal. Control items such as time of day or related timing functions may be entered into storage in this way. Variable data which may be required for computation is stored in the random access memory 73.

The microprocessor 70 utilizes a clock 70' as the time base for all internal functions and compares the value of the various inputs with established limits set in the memory. Off normal values provides an alarm output indicating an abnormal or undesired condition of operation. The display 81 which may also include a data printer can provide data in response to a code introduced by the keyboard 80 so that an operator can check on any specific condition of the operation as for instance the ultraviolet intensity of each lamp.

The output from the microprocessor is then converted by the digital to analog convertor 83 and functions through the multiplexing gates 84 to constantly adjust the magnitude of the voltage fed to each of the lamps 44 through 47.

In addition to the factors introduced into the computer as illustrated in FIG. 8 for control of radiation intensity, other factors such as the deposit of materials on the quartz elements 32 surrounding the lamps can be introduced as constants or measured values and may be utilized to operate a suitable cleaning mechanism which would automatically remove deposits periodically. This may be an important factor in many applications in as much as it affects the transparency of the tubular elements 32.

To illustrate the importance of this invention, let it be assumed that a sterilizer is required under ideal conditions to sterilize a clear liquid having a fixed flow of a hundred liters per minute (38,000 gallons per day). Under these conditions, the input power required would be approximately 200 watts or 4.8 KW/hrs. per day. However, it is well recognized that ideal conditions do not always exist and that a variation in turbidity, less than ideal operating conditions including older lamps, unclean lamp protecting elements and off optimum temperature can require as much as 75 times the power required for the ideal case even assuming constant flow. Under these conditions, as much as 15 KW input would be required or approximately 360 KW/hrs. per day. In this one instance, it can be seen that through the control of the intensity of the radiation to provide only that radiation required for sterilization of the liquid under actual conditions that a material saving in power can be effected. It also follows that under these conditions lamp life would be greatly extended.

The foregoing example while being an extreme case nevertheless emphasizes the significant gain even under other conditions. When treating waste water for instance, the influent conditions may vary from hour to hour, daily or seasonally. If all factors remain the same and only the influent turbidity changes from an absorption coefficient of 0.005 to 0.5, a ten-fold energy difference would be experienced. The foregoing assumes a constant flow rate though in actual practice the flow rate will also vary materially and this of course would greatly further modify the power requirements. If conductivity, such as metallic content, pH and the like of the water, should change, this would further increase the ratio of power required between the so-called ideal and worst conditions. Under these combined circumstances, it is possible to have an energy ratio as great as 15,000 to 1 though in practical application such an energy ratio would be excessive for economic and size reasons and therefore practical limits would be imposed on permissible variables. Notwithstanding such limits, significant gains in efficiency of one or two orders of magnitude can readily be realized over known methods and apparatus. From the foregoing, it becomes eminently apparent why known large volume devices and methods, all of the brute force type, are extremely limited in their application to low flow, clear liquid systems and therefore under more severe conditions are not cost effective as a means for practical disinfection or sterilization as evidenced from the following Table I and FIG. 9 of the drawings.

TABLE I

| Variable | Range | Worst Case Maximum Power | Nominal | Ideal Case Minimum Power | Nominal Range | Maximum Range |
|---|---|---|---|---|---|---|
| Lamp life | 10,000 hours | 100% | 90% | 80% | 1.11:1 | 1.25:1 |
| Lamp temperature | 60.8° F. to 104° F. | 100% | 50% | 33% | 2:1 | 3:1 |
| Ultraviolet transmission jacket | 100% to 50% | 100% | 75% | 50% | 1.33:1 | 2:1 |
| Flow rate | 100% to 25% | 100% | 35% | 5% | 2.85:1 | 20:1 |
| Influent Turbidity | Absorption Coef. .005 to 0.5 | 100% | 25% | 10% | 4:1 | 10:1 |
| Influent Chemistry | .005 to 0.5 | 100% | 25% | 10% | 4:1 | 10:1 |
| TOTAL ENERGY RATIO | | | | | 135:1 | 15000:1 |
| ENERGY RATIO WITH CONSTANT FLOW AND INFLUENT CHEMISTRY | | | | | 12:1 | 75:1 |

Table I lists a plurality of variables such as lamp life etc., the total range of each said variables and the energy required under the worst, nominal and ideal conditions. The worst case requires the use of maximum available energy to properly sterilize a liquid under the most adverse conditions that may be experienced in a specific application. The ideal case requires the least power while the nominal case represents the normal changes of the variables from the worst case that could be expected in actual practice. The percentages shown for each of the variables indicates that part of the total power required in each of the three cases if all other variables remained constant. Thus, if the flow rate dropped from an estimated maximum flow to a nominal or average flow the energy requirement would be reduced to 35% of the maximum energy required. The final columns in the table show the power ratio for each of the variables with the column entitled "Nominal Range" being the ratio of the worst case to the nominal case and the column entitled "Maximum Range" being the ratio of the worst case to the ideal case.

The energy reductions indicated for the variables are conservative estimates and in the case when all of the variables change so that energy requirements are reduced from the worst case to the nominal case, the resultant energy is reduced to 1/135 of the energy required for the worst case. In many applications, extremely wide variations can be experienced in each of the variables. This may occur chiefly in industrial plants where waste water is generally filtered and then sterilized prior to disposal. In such cases, composition of the water, flow rate, solid content and the like can vary over extremely wide limits and at greatly varying periodicities. Should the ideal case exist for even short periods of time, it would be possible to reduce the energy requirements to 1/15000 of the power required for the worst case. It is therefore evident that in any application, including the treatment of drinking water, variations in flow and water characteristics will be experienced with the result that this invention will effect savings in energy not heretofore considered possible or even probable.

Taking an even more conservative view of conditions that may exist in actual practice and assume that liquid flow and chemistry remain constant, a 12:1 gain in energy savings is realized with variations from the worst case to the nominal case while the energy ratio from the worst case to the ideal case is 75:1. Since the apparatus in accordance with the invention functions to change energy requirements far more rapidly than changes in any of the variables can occur, maximum operating efficiency is maintained at all times. It is therefore evident that with this invention substantial energy savings can be effected and at the same time effective sterilization attained.

A typical example of the power demand to meet variations normally experienced in the use of ultraviolet radiation for the sterilization of liquids is shown in FIG. 9. The illustrated graph is hypothetical but nevertheless closely approximates conditions existing in actual applications wherein the flow rate and liquid quality are constant. For the first hour or more of operation, it is assumed that the influent is ideal, that is, relatively clear. This portion of the graph is denoted by A and it will be noted that even under such conditions small variations such as turbidity and the like are present. These variations are sensed by the apparatus in accordance with the invention and the energy imparted to the liquid follows these variations and accordingly affords some energy reduction.

Section B of the graph illustrates the increase of energy required for an increase in turbidity which in this case is approximately 1800 watts. Section C of the graph indicates a further two or three fold increase in energy required as a result of deposits on the protective jackets surrounding the lamps after several hundreds of hours of operation. Section D of the graph represents the increase in power, approximately two-fold, should lamp temperature drift to either side of a normal value for most efficient lamp operation. At this point, the power requirements have now increased from 200 watts to over 10,000 watts as the result of changes in only three variables. Section E of the graph shows the probable increase in power required due to aging of the lamps and possibly other changes with the result that a maximum constant power of 15,000 watts would be required to insure proper sterilization in prior art uncontrolled systems.

Section F of the graph shows a reduction in power as the result of adjustment of lamp temperature. It will be observed that the mere adjustment of lamp temperature reduces power from a value in excess of 10,000 watts to below 4,000 watts. Section G of the graph represents a gradual increase in power because of lamp aging and corresponds essentially to graph section E.

It will be observed that the repetitive variations occurring at section A of the graph shown in FIG 9 actually continue throughout the entire graph. Since, as pointed out above, the apparatus in accordance with the invention senses these variations more rapidly than they occur, the energy imparted to the liquid will also fluctuate and provide the required radiation intensity to effect the desired sterilization. Thus, a further saving of energy is realized throughout the entire process.

In the foregoing description of the invention, for ultraviolet lamps are employed for sterilization of the fluid and under these conditions the flow rate would normally be at a reduced value and limitations would of course be placed on turbidity and conductivity. It is evident, however, that apparatus in accordance with the invention may employ any number of ultraviolet radiating sources and that the sources may be of any desired size and configuration. For instance, in the treatment of turbid waste water, it is conceivable that hundreds of ultraviolet lamps would be employed with each of the lamps being controlled in accordance with the invention in order to insure reliable operation of the apparatus. At the same time, should conditions occur which would not require operation of all of the lamps, the apparatus would automatically inactivate one or more lamps not required to effect sterilization.

It is apparent from the foregoing that the lamps 44 through 47 can be controlled in a variety of ways. One procedure is to provide for the simultaneous control of the intensity of all lamps in accordance with fluid flow and characteristics as previously described. A more important procedure which affords a significant improvement in efficiency and provides greater latitude of operation involves independent control of each lamp. With such an arrangement, the intensities of the lamps are individually controlled whereby one lamp, for instance, may be at a high intensity while the remaining lamps may be at the same or different reduced intensities. Under these conditions, the apparatus can handle, more precisely, a far wider range of fluid conditions and thus effect a further material improvement in efficiency.

The invention heretofore described provides for the control of the radiation intensity in response to fluid characteristics and flow relative to monitored operating conditions of the lamps. In certain applications, it may be desirable to maintain substantially uniform ultraviolet radiation intensity and modify the fluid flow in response to fluid characteristics. For this purpose, an electrically operated flow control valve 110 (FIGS. 1 and 8), having control conductors 111, is coupled to the inlet conduit 12. The flow control valve 110 is connected by means of a driving amplifier 112 to the multiplex gates 84. With this arrangement and by appropriately programming the control 71, fluid characteristics as well as the condition of the lamps and the intensity of the radiation penetrating the fluid will function to control the fluid flow rate to insure proper sterilization of the fluid.

It is well known that chemical disinfection using chemicals such as chlorine for instance is widely used in industry and generally constitutes the principal means for disinfecting drinking water. Not only is chlorine relatively expensive and the apparatus for controlling the admission of chlorine into a liquid system costly, but chlorine in quantities presently required materially and adversely affects the taste of drinking water and in addition has been found to be a cancer causing agent. Chlorine is also generally considered a disinfecting agent rather than a sterilizing agent and thus has little, if any, affect on some viruses. It has been suggested that it is possible to utilize both ultraviolet sterilization and chemical disinfection which utilizes the advantages of both systems, namely sterilization and continued disinfection. With this invention, it has been found that the cost of water treatment utilizing both ultraviolet radiation and chemical treatment is materially below the cost of either system alone. Based on information presently available, it has been determined that with a combined system chlorine requirements can be reduced to about one-tenth to one-fifteenth of the normal requirements and energy requirements for ultraviolet radiation to about one-tenth to one-quarter of the energy normally required. Thus by using the combination of the two systems with this invention, a profound synergistic is realized in that the cost can be reduced to the order of 20 to 25 percent of the cost of either system alone.

To achieve this end, an electrically operated chlorine control valve 113 as shown in FIGS. 1 and 8 is connected by means of conductors 115 to the multiplex gates 84 through a driver amplifier 114. By appropriately programming the control 71, precise amounts of chlorine can be fed to the fluid and at the same time coordinated with the ultraviolet radiation to achieve the most economical operating conditions for fluid characteristics and flow.

While the term "sterilization" is broadly defined as the destruction of all living organisms, the use of the term "sterilization" herein is also intended to include the reduction of at least certain living organisms to a predetermined maximum count as well as disinfection which in the general sense means the total or partial destruction of harmful living organisms.

While only one embodiment of the invention has been illustrated and described, it is apparent that alterations, changes and modifications may be made without departing from the true scope and spirit thereof.

What is claimed is:

1. The method of destroying undesirable microorganisms in a fluid utilizing ultraviolet radiation comprising passing said fluid in proximity to at least one electrically energized ultraviolet radiation source, measuring at least selected physical characteristics of said fluid including turbidity and the rate of flow of said fluid and operating conditions of said source including source intensity and radiation absorption and periodically modifying the relationship of at least said rate of flow to said source intensity in accordance with said physical characteristics to continuously impart a predetermined quantity of energy to said fluid per unit volume thereof, said quantity of energy being predetermined based on said measured physical characteristics to provide the desired destruction of micro-organisms.

2. The method according to claim 1 including the step of filtering the energy fed to said radiation source to remove high frequency energy pulses such as switching transients and the like.

3. The method according to claim 1 wherein said measured physical characteristics of the fluid further includes electrical conductivity and temperature.

4. The method according to claim 1 including the step of modifying the energy imparted to said fluid by said source in accordance with changes in the physical characteristics and flow of said fluid.

5. The method according to claim 1 wherein said energy imparted to said fluid is maintained substantially constant and said fluid flow is modified in accordance with changes in fluid characteristics.

6. The method according to claim 1 including the steps of feeding a chemical disinfectant into said fluid and controlling the admission of said chemical disinfectant to maintain a preselected relationship between chemical flow and the ultraviolet energy imparted to said fluid per unit volume of fluid.

7. The method of destroying undesirable living organisms in a fluid according to claim 1 including the steps of passing said fluid in proximity to at least one electrically energized ultraviolet radiation source, continuously measuring the temperature of said source and continuously adjusting said temperature to optimize the efficiency of said source.

8. The method according to claim 1 wherein said radiation source is in the form of an elongated tube surrounded by a radiation transparent tube and measuring said source intensity at the outer surface of said radiation transparent tube.

9. The method according to claim 8 which further includes the steps of measuring the temperature of said source, and the radiation produced by said source within a selected band of wavelengths and modifying the operation of said source to effect the generation of the desired intensity within said selected band of wavelengths.

* * * * *